United States Patent [19]

Keng

[11] Patent Number: 4,962,026

[45] Date of Patent: Oct. 9, 1990

[54] PROCESS FOR THE PRODUCTION OF PANOSYL DERIVATIVES

[75] Inventor: Jiun G. Keng, Darien, Ill.

[73] Assignee: Enzyme Bio-Systems, Ltd., Englewood Cliffs, N.J.

[21] Appl. No.: 907,554

[22] Filed: Sep. 15, 1986

[51] Int. Cl.$^5$ .................. C12P 19/16; C12P 19/44; C12P 19/14; C12N 9/28

[52] U.S. Cl. .................................. 435/98; 435/74; 435/202; 435/99

[58] Field of Search ............... 435/201, 98, 837, 202, 435/822, 74, 170, 193, 99

[56] References Cited

U.S. PATENT DOCUMENTS

| | | | |
|---|---|---|---|
| 3,878,819 | 4/1975 | Fukumoto et al. | 260/210 F |
| 4,219,571 | 8/1980 | Miyake | 426/52 |
| 4,469,791 | 9/1984 | Colson et al. | 435/253 |

FOREIGN PATENT DOCUMENTS 0164933 12/1985 European Pat. Off. .
0165002 12/1985 European Pat. Off. .

OTHER PUBLICATIONS

M.-E. David, et al, *Starch*, 39, 436-440 (1987), "Catalytic Properties of *Bacillus megaterium* Amylase".
Shimizu, et al, *Agric. Biol. Chem.*, 42, 1681-1699 (1978).

*Primary Examiner*—Elizabeth C. Weimar
*Assistant Examiner*—Irene Marx
*Attorney, Agent, or Firm*—Rockey and Rifkin

[57] ABSTRACT

This invention relates to an in vitro enzymatic process for the preparation of compounds containing the panosyl group. The panosyl group is transferred from a panosyl donor to a panosyl acceptor by means of an enzyme having panosyl transferase activity.

2 Claims, No Drawings

PROCESS FOR THE PRODUCTION OF PANOSYL DERIVATIVES

FIELD OF THE INVENTION

This invention relates to an in vitro enzymatic process for preparing molecules containing the panosyl group. The panosyl group is transferred from a panosyl donor to a panosyl acceptor to give a panosyl derivative of the panosyl acceptor. The transfer reaction is catalyzed by an enzyme having panosyl transferase activity.

BACKGROUND OF THE INVENTION

The transfer of a glucosyl group from one carbohydrate molecule to another is well known. This transfer is catalyzed by a number of different glucosyl transferase enzymes. Similarly, there are a number of fructosyl transferase enzymes which will transfer the fructosyl group from one carbohydrate molecule to another. However, the transfer of the more complex trisaccharide group, the panosyl group, from one carbohydrate molecule to another has never been reported.

It has now been discovered that certain enzymes do possess the ability to transfer the panosyl group from a carbohydrate molecule to another molecule. The second molecule is a carbohydrate or a molecule containing a carbohydrate moiety. By means of such enzymes, it is possible to produce new carbohydrate derivatives with unique properties. The reaction is particularly useful for modifying certain high-intensity sweeteners. Such modified sweeteners have improved water solubility and less bitter aftertaste. Carbohydrates modified in this manner are also less cariogenic than some simpler sugars.

SUMMARY OF THE INVENTION

In accordance with the present invention, there is provided for the first time an in vitro enzymatic process for transferring the panosyl group from a panosyl donor to a panosyl acceptor, said panosyl acceptor comprising a carbohydrate or a molecule containing a carbohydrate moiety, which comprises allowing a panosyl transferase enzyme to react on an aqueous solution containing the panosyl donor and the panosyl acceptor for a sufficient time to produce a panosyl derivative of the panosyl acceptor.

DETAILED DESCRIPTION OF THE INVENTION

For the purposes of this specification, the following definitions are provided for the various terms used herein:

1. Panosyl Group

The term "panosyl group", as used herein, refers to the group O-alpha-D-glucopyranosyl-(1→6)-O-alpha-D glucopyranosyl-(1→4)-alpha-D-glycopyranosyl.

2. Panosyl Donor

The term "panosyl donor", as used in this application, refers to a molecule which is capable of furnishing the panosyl group for transfer to another molecule.

3. Panosyl Acceptor

The term "panosyl acceptor", as used herein, refers to any carbohydrate molecule, or molecule containing a carbohydrate moiety, capable of combining with the panosyl group to form a new molecule.

4. Panosyl Transferase Enzyme

The term "panosyl transferase enzyme", as used herein, refers to any enzyme that catalyzes transfer of the panosyl group from a panosyl donor to a panosyl acceptor, and includes the enzyme preparation showing alpha-amylase activity derived from *Bacillus megaterium*, NCIB 11568.

The reaction of this invention involves the transfer of panose from a donor, such as pullulan, to an acceptor, such as glucose, to form the panosyl derivative of the acceptor. When the acceptor is glucose, the product is 4-panosylglucose.

Any enzyme or enzyme system having panosyl transferase activity can be used in this invention. These include the amylases having panosyl transferase activity obtained from *B. megaterium* (*Bacillus megaterium*) and *T. vulgaris* (*Thermoactinomyces vulgaris*). A particularly useful panosyl transferase is the one produced by *B. megaterium*, Strain NCIB 11568, described in U.S. Pat. No. 4,469,791. The gene coding for the production of this enzyme has been transferred into a strain of *B. subtilis* (*Bacillus subtilis*) giving a microorganism which is a better producer of the enzyme. The strain of *B. subtilis* containing the amylase gene, NCIB 11980, is described in the published European patent application bearing Publication No. 0 165 002.

A panosyl donor useful for carrying out the process of the present invention is the polysaccharide pullulan. Other useful donors include partially-hydrolyzed pullulan molecules and starch fragments which contain multiple panose units.

Panosyl acceptors suitable for use in the process of this invention are molecules containing a pyranose structure with the same configuration of the C2-, C3-, and C4-hydroxyl groups as D-glucopyranose. In the process of this invention, the panosyl group becomes attached to the panosyl acceptor molecule by the formation of a glycosidic linkage at C4 of the acceptor. Suitable acceptors include D-glucose, L-sorbose, D-xylose, sucrose, maltose, and alpha-methylglucoside.

The reaction of this invention is particularly useful for making derivatives of high-intensity glycoside sweeteners. Such sweeteners include stevioside, hesperetin dihydrochalcone-7-glucoside, and naringenin-7-glucoside. These sweeteners have the disadvantage of extremely low water solubility. The panosyl derivatives are substantially more soluble in water than are the parent sweeteners but are still very sweet. Furthermore, the increased water solubility appears to correlate with the reduction of bitter aftertaste which is inherent in the parent compounds.

The conditions used for carrying out the panosyl transferase reactions of the present invention are those suitable for the enzyme involved. When *B. megaterium* amylase is used, the temperature can vary from 40° C. to 60° C. and the pH from 4.5 to 6.5. The transglycosylation is carried out by incubating a solution of the panosyl donor and the panosyl acceptor in the presence of the panosyl transferase enzyme for a sufficient time to allow maximum formation of the panosyl derivative. It is convenient to follow product formation by means of thin-layer chromatography.

Purification of the panosyl transferase enzyme is not necessarily required before the enzyme is used in the process of this invention. A solution of the crude enzyme can be obtained by separating the broth from the cell debris and other solids left after growing the organism which produces the enzyme. If necessary, the crude transferase enzyme may be purified by any known method before its use. Conventional purification techniques, such as salting out with an inorganic salt or precipitating with an organic precipitant, such as alcohol or acetone, may be used.

The panosyl transferase enzyme can be immobilized on suitable supports and the immobilized enzyme may be used repeatedly in batchwise systems or in continuous systems.

The panosyl transferase enzyme hydrolyzes pullulan to panose in the absence of a suitable panosyl acceptor molecule. This fact is used to determine the activity of the enzyme which is measured as pullulan hydrolase activity. A 2% solution of pullulan is treated with the enzyme solution at 50° C., pH 5.5, and the release of panose is determined by reduction of ferricyanide using maltose as a standard. This general method is described by Robyt, et al, *Anal. Biochem.*, 45, 517 (1972). One unit of enzyme activity is defined as the amount of enzyme which liberates 1 micromole of panose per minute under the test conditions.

The following examples further describe the embodiments of this invention. All percentages are by weight unless expressly stated to be otherwise.

EXAMPLE 1

To a solution of 0.5 g of pullulan and 2.0 g of glucose in 10 ml of 50 mM acetate buffer at pH 5.5 and 50° C. was added 7.2 units of panosyl transferase enzyme. The panosyl transferase enzyme was a crude enzyme preparation produced by the fermentation of a strain of *B. subtilis*, NCIB 11980, which contains a plasmid having the *B. megaterium* amylase gene. The cell-free broth was used without further purification. The formation of panosylglucose (DP4) was followed by thin-layer chromatography using a solvent system of chloroform:methanol:water (30:20:4). Reaction products were visualized with 5% $H_2SO_4$ in ethanol. Product distribution as a function of time was determined by high-performance liquid chromatography (HPLC) using HPX-42A cation-exchange resin and eluting with pure water at 80° C.

The reaction was repeated using sucrose and alpha-methylglucoside in place of glucose as the panosyl acceptor. A control reaction was also run in which no panosyl acceptor was added.

The HPLC results given in Table I show that glucose, sucrose, and alpha-methylglucoside are all suitable panosyl acceptors giving respectively 86.5%, 77.1%, and 92% conversion of pullulan to the corresponding derivative. Carbon-13 NMR analysis showed that the panosyl group was attached to Carbon 4 (C4) of the glucose moiety of the panosyl acceptor. The pullulan hydrolyzing activity of the enzyme was observed in the comparative test run where no panosyl acceptor was present.

TABLE I

| | | PANOSYL TRANSFER FROM PULLULAN TO PANOSYL ACCEPTORS | | | | | |
|---|---|---|---|---|---|---|---|
| | Time | Area % by HPLC | | | | | |
| Acceptor | (hr) | DP1[a] | DP2 | DP3 | DP4 | DP5 | DP6+ |
| None[b] | 0 | 0.9 | — | 0 | — | — | 99.1 |
| | 0.33 | 1.0 | — | 5.9 | — | — | 93.0 |
| | 1 | 1.0 | — | 15.2 | — | — | 83.7 |
| | 17 | 0.8 | — | 91.7 | — | — | 7.5 |
| Glucose | 0 | 82.9 | — | 0 | 0 | — | 17.1 |
| | 0.33 | 78.6 | — | 0 | 12.2 | — | 9.8 |
| | 1 | 77.5 | — | 0.1 | 14.3 | — | 8.1 |
| | 17 | 78.1 | — | 3.8 | 14.8 | — | 3.3 |
| alpha- | 0 | 82.3 | — | 0 | 0 | — | 17.7 |
| Methyl- | 0.33 | 77.2 | — | 0 | 13.0 | — | 9.8 |

TABLE I-continued

| | | PANOSYL TRANSFER FROM PULLULAN TO PANOSYL ACCEPTORS | | | | | |
|---|---|---|---|---|---|---|---|
| | Time | Area % by HPLC | | | | | |
| Acceptor | (hr) | DP1[a] | DP2 | DP3 | DP4 | DP5 | DP6+ |
| glucoside | 1 | 76.6 | — | 0 | 16.3 | — | 7.1 |
| | 17 | 78.1 | — | 6.4 | 12.8 | — | 2.7 |
| Sucrose | 0 | — | 84.3 | 0 | — | 0 | 15.7 |
| | 0.33 | — | 79.9 | 0.8 | — | 7.5 | 11.8 |
| | 1 | — | 79.6 | 0.9 | — | 9.2 | 10.3 |
| | 17 | — | 79.9 | 3.4 | — | 12.1 | 4.6 |

[a]DP1 is a monosaccharide, DP2 a disaccharide, etc., and DP6+ are the oligosaccharides having 6 or more monosaccharide units.
[b]Comparative test, not an example of this invention.

The DP4 material obtained when glucose is the acceptor is 4-panosylglucose. The DP4 material obtained when alpha-methylglucoside is the acceptor is 4-panosyl-alpha-methylglucoside, a new composition of matter. This material may be isolated from the reaction mixture by means of preparative HPLC using the same general resin and elution technique as used for the analysis of the mixture. The DP5 material obtained when sucrose is the acceptor is the panosyl derivative of sucrose attached at Carbon 4 of the glucose moiety of the sucrose molecule. This is also a new composition of matter.

EXAMPLE 2

The general procedure of Example 1 was repeated using the alpha-amylase from *T. vulgaris*, Strain R-47, except that the reaction was run at pH 4.5 and 60° C. Glucose was used as the acceptor and a comparative test was run using no acceptor. *T. vulgaris*, Strain R-47, was deposited with the American Culture Collection, Rockville, Md., as ATCC No. 53532, under the provisions of the Budapest Treaty and is available as provided in that Treaty.

The amylase from *T. vulgaris* and its ability to hydrolyze pullulan were reported by Shimizu, et al, *Agric. Biol. Chem.*, 42, 1681–1688 (1978). The panosyl transferase enzyme was adsorbed on diatomaceous earth by mixing cell-free fermentation broth with 2 volumes of acetone in the presence of 1% (w/v) diatomaceous earth. This solid containing adsorbed enzyme was used in this and subsequent examples where the *T. vulgaris* transferase is specified.

Comparative tests were also run with the amylase enzyme from *B. megaterium* used in Example 1 except that in this experiment the reaction was run at pH 4.5 and 60° C. The results given in Table II show that the amylase from *T. vulgaris* catalyzes the transfer of the panosyl group from pullulan to glucose. However, under the conditions of this experiment, it gives somewhat lower yields of 4-panosylglucose and somewhat higher yields of panose (due to hydrolysis of the pullulan) than does the amylase from *B. megaterium*.

TABLE II

| | | COMPARISON OF TRANSFERASE ACTIVITY | | | |
|---|---|---|---|---|---|
| | | Area % by HPLC | | | |
| | | No Acceptor[b] | | Glucose Acceptor | |
| Time | Carbo- | B. | T. | B. | T. |
| (hr) | hydrate[a] | megaterium | vulgaris | megaterium | vulgaris |
| 0 | DP1 | 0.8 | 0.9 | 82.3 | 81.8 |
| | DP2 | — | — | — | — |
| | DP3 | — | — | — | — |
| | DP4 | — | — | — | — |
| | DP5 | — | — | — | — |
| | DP6 | — | — | — | — |

TABLE II-continued

COMPARISON OF TRANSFERASE ACTIVITY

| Time (hr) | Carbo-hydrate[a] | Area % by HPLC | | | |
|---|---|---|---|---|---|
| | | No Acceptor[b] | | Glucose Acceptor | |
| | | B. megaterium | T. vulgaris | B. megaterium | T. vulgaris |
| | DP7+ | 99.2 | 99.1 | 17.7 | 18.2 |
| 17 | DP1 | 0.8 | 1.6 | 77.0 | 76.7 |
| | DP2 | — | 2.7 | — | 0.7 |
| | DP3 | 51.5 | 94.0 | 3.5 | 9.7 |
| | DP4 | — | — | 15.7 | 12.0 |
| | DP5 | — | — | — | — |
| | DP6 | 25.3 | 1.7 | 0.5 | 0.3 |
| | DP7+ | 22.4 | — | 3.3 | 0.6 |

[a]DP1 is a monosaccharide, DP2 is a disaccharide, etc., and DP7+ are the oligosaccharides having 7 or more monosaccharide units.
[b]Comparative test, not an example of this invention.

EXAMPLE 3

Preparation of Panosyl Stevioside

A solution of 2 g of pullulan and 1 g of stevioside (Sigma Chemical Co.) in 100 ml of 50 mM acetate buffer at pH 5.5 was heated with 76 units of *B. megaterium* panosyl transferase for 3 hours at 50° C. The mixture was boiled for 10 minutes to inactivate the enzyme before it was filtered, concentrated 8-fold under reduced pressure and freeze-dried. Thin-layer chromatography showed that the main products were panosyl stevioside and panose formed by hydrolysis of the excess pullulan used.

This product was compared with a control mixture consisting of two parts of panose and one part unmodified stevioside. The mixture containing panosylstevioside was eight times more soluble in water at 25° C. A ten-member taste panel rated the mixture containing panosylstevioside as somewhat less sweet and as having distinctly less bitter aftertaste than the mixture containing unmodified stevioside.

EXAMPLE 4

The process of Example 3 was repeated using hesperetin dihydrochalcone glucoside (HDG) in place of stevioside. The HDG is prepared from hesperidin by the general procedures of U.S. Pat. No. 3,429,873. It was necessary to dissolve 1 g of the HDG in 20 ml of warm ethanol before mixing with the acetate buffer solution of pullulan. Although the product was four times more soluble in water at 25° C., it was not as sweet as the control mixture containing unmodified HDG.

Thus, it is apparent that there has been provided, in accordance with the invention, an in vitro enzymatic process for transferring the panosyl group from a panosyl donor to a panosyl acceptor. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. An in vitro enzymatic process for preparing a panosyl derivative of a panosyl acceptor which comprises allowing a panosyl transferase enzyme to react on an aqueous solution containing pullulan and said panosyl acceptor for a sufficient time to produce a panosyl derivative of said panosyl acceptor, wherein the panosyl acceptor is selected from the group consisting of D-glucose, sucrose, alpha-methylglucoside, stevioside and hesperetin dihydrochalcone glucoside, wherein the enzyme is the pullulan hydrolyzing alpha-amylase produced by *Bacillus megaterium* NCIB 11568 or *Bacillus subtilis* NCIB 11980, which exhibits panosyl transferase activity.

2. An in vitro enzymatic process for preparing a panosyl derivative of a panosyl acceptor which comprises allowing a panosyl transferase enzyme to react on an aqueous solution containing pullulan and said panosyl acceptor for a sufficient time to produce a panosyl derivative of said panosyl acceptor, wherein the panosyl acceptor is selected from the group consisting of D-glucose, sucrose, alpha-methylglucoside, stevioside and hesperetin dihydrochalcone glucoside, wherein the enzyme is the pullulan hydrolyzing alpha-amylase produced by *Thermoactinomyces vulgaris* R-47, ATCC 53532, which exhibits panosyl transferase activity.

* * * * *